United States Patent [19]

Franke

[11] 4,188,537
[45] Feb. 12, 1980

[54] DENTAL APPARATUS FOR X-RAY DIAGNOSIS

[75] Inventor: Kurt Franke, Erlangen, Fed. Rep. of Germany

[73] Assignee: Siemens Aktiengesellschaft, Berlin & Munich, Fed. Rep. of Germany

[21] Appl. No.: 834,314

[22] Filed: Sep. 19, 1977

[30] Foreign Application Priority Data

Oct. 15, 1976 [DE] Fed. Rep. of Germany ....... 2646638

[51] Int. Cl.² .............................................. G03B 41/16
[52] U.S. Cl. ........................... 250/416 TV; 250/439 P; 250/505
[58] Field of Search ................... 250/401, 402, 416 R, 250/416 TV, 505, 514, 358 R, 358 P, 359, 360, 439 P

[56] References Cited

U.S. PATENT DOCUMENTS

| | | | |
|---|---|---|---|
| 3,622,785 | 11/1971 | Irwin | 250/416 TV |
| 3,766,387 | 10/1973 | Heffan | 250/416 R |
| 3,780,291 | 12/1973 | Stein | 250/416 TV |
| 3,790,799 | 2/1974 | Stein | 250/416 TV |
| 4,021,672 | 5/1977 | Franke | 250/402 |
| 4,031,401 | 6/1977 | Jacob | 250/514 |

*Primary Examiner*—Craig E. Church
*Attorney, Agent, or Firm*—Hill, Van Santen, Steadman, Chiara & Simpson

[57] ABSTRACT

A dental apparatus for x-ray diagnosis, which apparatus has a x-ray tube and a carrier for a radiation receiver disposed on a unit for rotation about a support for holding a head of a patient, characterized by the radiation receiver including transducer means for forming electrical signals corresponding to a measured radiation intensity, a data processing installation having means for storing the measured radiation intensity for one exposure sequence and means for creating a survey image from the stored information and displaying the image on a display device. The transducer means may be a plurality of detectors placed on a vertically extending line or a single detector which is moved vertically along a line during the x-ray process so that a vertical scan is obtained.

3 Claims, 3 Drawing Figures

DENTAL APPARATUS FOR X-RAY DIAGNOSIS

BACKGROUND OF THE INVENTION

The present invention is directed to a dental x-ray diagnosis installation or apparatus which has a head support for holding a patient's head in a fixed position and unit which includes an x-ray tube and a carrier for a radiation receiver and is rotatable about a vertical axis with the carrier and x-ray tube rotating about the head support so that a survey image, such as of a jaw, is produced.

PRIOR ART

Basically two types of x-ray apparatus are known for preparing dental survey photographs. One type of apparatus utilizes an x-ray tube having an anode which is inserted into the patient's mouth. The x-ray film is then held externally against the patient's face and in order to prepare a photograph, the jaws are radiated from the interior of the mouth to the exterior.

The second known type of apparatus is an x-ray diagnostic installation of the type which has a unit rotatable on a vertical line which unit includes an x-ray tube and an x-ray receiver comprising an x-ray film holder. The rotatable unit moves around a support which holds the head of the patient. In order to prepare a survey tomogram of the teeth or jaw of the patient's head, the patient's head is held by the support and x-ray tube and film holder move about the patient's head. Both the x-ray tube and the film are rotated as a unit about a vertical axis so that the x-rays always impinge on the teeth at a right angle and the space between the row of teeth and the film is maintained constant. During the course of the exposure, the x-ray tube and film moved about the patient's head and the teeth are successively reproduced on the film so that a tomogram of a curved plane similar to the teeth or jaw of the patient is produced.

One of the drawbacks of both known types of x-ray diagnostic equipment is that only film exposures can be produced. Therefore it is impossible to produce dental x-ray images in another manner for example by a television video unit. Thus, in order to analyze the exposure, it is always necessary to first develop the exposed film.

SUMMARY OF THE INVENTION

The present invention is directed to providing an apparatus for x-ray diagnosis in which the x-ray tube and carrier for a radiation receiver rotate as a unit around a patient's head with the apparatus displaying the images on a video unit or an equivalent reproduction device.

To accomplish this task, the present invention is directed to an improvement in an apparatus for x-ray diagnosis which apparatus includes a head support for holding a head of a patient in a given position, and a unit having an x-ray tube and carrier for a radiation receiver, said unit being rotatable about a vertical axis with the x-ray tube and the carrier rotating about the head support. The apparatus includes an operative sequence mechanism for fixing the exposure time in advance as the apparatus prepares a survey image. The improvement comprises the radiation receivers including transducer means for measuring radiation intensities and forming electrical signals corresponding to measured radiation intensities, said transducer means being connected to a data processing installation having means for storing the electrical signals for one exposure sequence and means for creating a survey image from the stored electrical signals, and the apparatus includes an image reproduction device connected to the data processing installation for displaying the created survey image.

DESCRIPTION OF THE PREFERRED EMBODIMENTS

Figure 1:
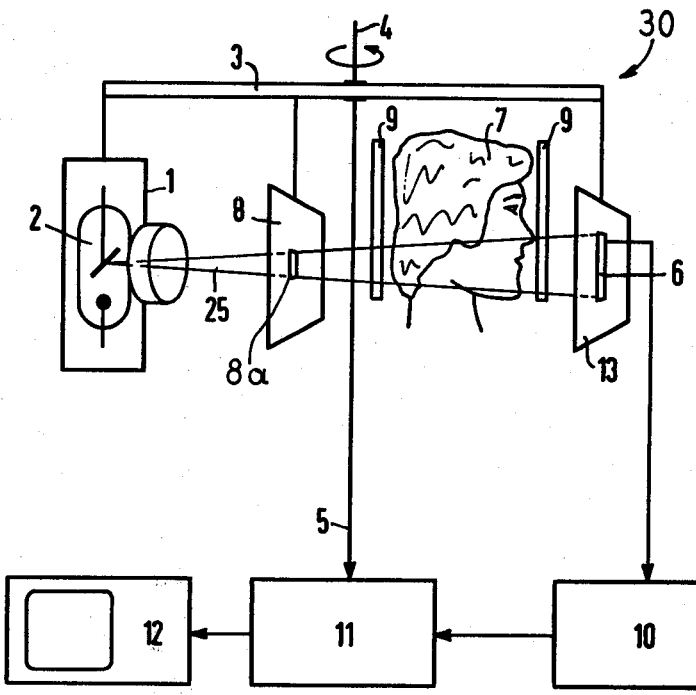
FIG. 1 is a schematic illustration of the embodiment of the present invention.

The principles of the present invention are particularly useful in a dental x-ray diagnostic apparatus generally indicated at 30. The apparatus 30 like known diagnostic apparatus has a rotatable unit or support 3, which on one end has a housing 1, which contains an x-ray tube 2. On the other end, the support 3 has a radiation receiver which is supported on or adjacent to a carrier or diaphragm 13. The apparatus 30, also, includes a support means such as member 9 for holding a head 7 of a patient in a desired position between x-ray tube 2 and carrier 13. The unit 3 will rotate on a vertical axis as illustrated by element 4 in such a manner that the radiation receiver will maintain the desired constant spacing from the jaw of the patient 7 and the beam of x-rays from tube 2 will strike each of the teeth successively at right angles thereto. The means for rotating unit 3 in this manner is conventional.

The improvement of the present invention is that the apparatus 30 instead of having a film holder for the carrier and film for the radiation receiver has a plurality of radiation detectors 6 which are transducer means for measuring radiation intensity and creating electrical signals corresponding to the measured radiation intensities. The detectors 6 are aligned on a vertical line with the number of detectors being selected according to the desired image resolution. In addition, a diaphragm 8, which has a slot-like aperture 8a, is secured to the support 3 between the x-ray tube 2 and the head support 9. Thus, due to the slot-like aperture 8a, the x-ray beam 25 which penetrates the jaw of the patient 7 will have a rectangular cross section with the major axis extending in the vertical direction to fall on the detectors 6 of the radiation receiver area.

Each of the detectors 6 creates an electrical signal corresponding to the particular radiation intensity being detected. Electrical signals of each of the detectors of the radiation receiver 6 are applied to a data processing unit which consists of a memory 10 and a conversion unit 11. Connected to an output of the conversion unit 11 is a display device, for example, an electronic video unit 12.

The diaphragm 13, which supports the radiation receivers or detectors 6, preferably is provided with a slit with the receivers disposed there behind so that they do not receive an excess radiation or radiation other than that of the beam 25.

To form an image of the patient's jaw, the x-ray tube 2 is switched and the unit 3 rotates about the axis 4 through an angle corresponding to the desired jaw area of the patient 7, which is to be photographed. The exposure time is preset in advance. In a predetermined angular position, for example, at every angle degree, the signals of the radiation receiver which is composed of the plurality of detectors 6 are fed into the memory 10 and interrogated by the latter. Since the rotation of the unit 3 is fed by line 5 to the unit 11, the interrogation is synchronized with the roation of the unit 3. Thus, all output signals of the radiation receivers 6 which are interrrogated at specific angular positions for the unit 3, produce a vertical image strip. An image is thus constructed from a number of vertical image strips by the data processing devices 10 and 11 and presented on the display device 12 such as a video unit. If a permanent record is desired, a photograph of the display on unit 12 can be made or a recording of the signals applied to unit 12 can be made.

Figure 2:
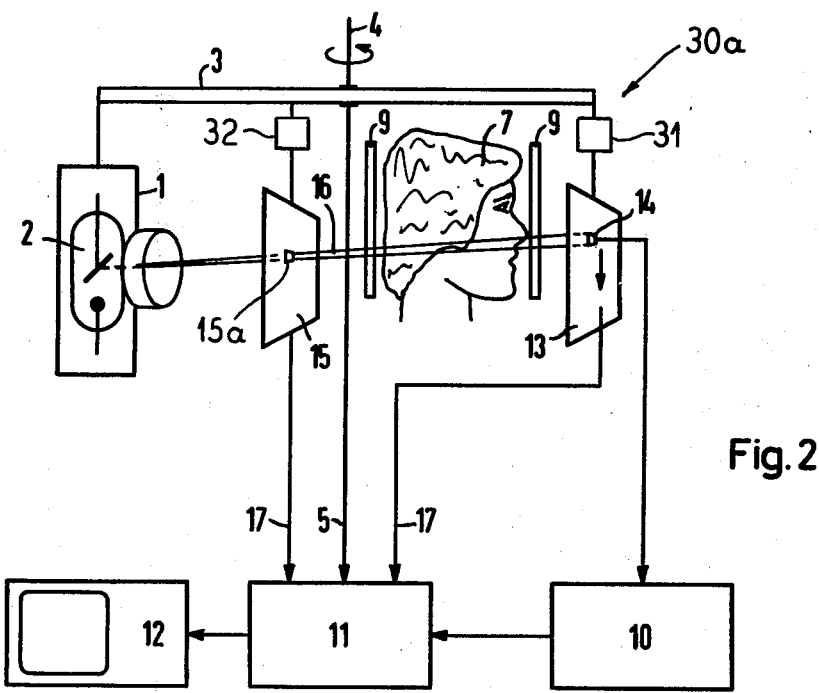
FIG. 2 is a schematic presentation of a second embodiment of the present invention.

The embodiment illustrated in FIG. 2 comprise an apparatus 30a in which each of the elements which are identical with the embodiment 30 of FIG. 1 are designated with the same reference number. As illustrated in FIG. 2, the apparatus 30a differs from the device 30 in that the radiation receiver is formed by a single detector 14, which receives the radiation penetrating an aperture in the diaphragm 13. For each angular position of the unit 3, the detector 14 is adjusted or shifted in a vertical direction by a predetermined amount, which corresponds to the length of the radiation detector 6 in FIG. 1. This displacement is schematically illustrated by displacement means 31 in the Figure. Instead of diaphragm 8, the apparatus 30a has a diaphragm 15, which has an aperture 15a so that only a tiny, thin x-ray beam 16, which has a cross section area of the area of the single detector 14 to cover the detector, can pass through the patient. Diaphragm 15 is also mounted for movement in a vertical direction by a device or displacement means 32 with the amount and direction of displacement of the diaphragm 15 and detector 14 being synchronized to form a vertical scan for each angle of rotation of the unit 3. The conversion unit 11 coordinates the interrogation of the output signal of the detector 14 with the movement of the detector 14 and the diaphragm 15 as indicated by the input arrows 17. The exposure cycle of the apparatus 30a is, therefore, such that each specific angular position of the unit 3, diaphragm 15 and detector 14 are displaced in a vertical direction by a desired amount corresponding to the image zone to be scanned. Then there is a rotational movement through a predetermined angle for example 1° and then there is another vertical scan or displacement. The rotational movement and vertical displacement thus follow in succession until the whole area of the patient 7, which is to be x-rayed, is scanned. The output signal of the detector 14 is then interrogated by the memory 10 and the x-ray image which is created or calculated in a data processing unit 10 and 11 will be displayed on display 12 as in the previous embodiment.

Figure 3:
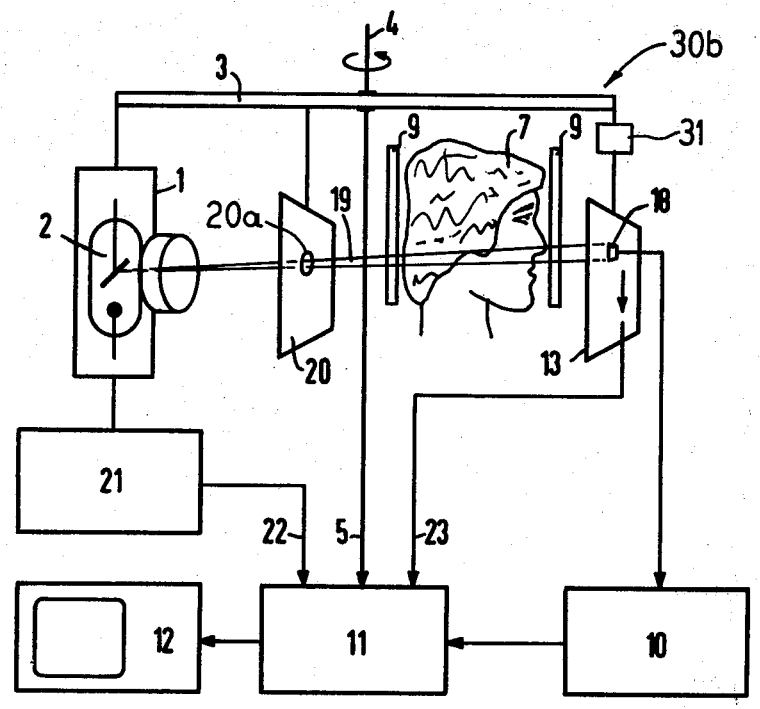
FIG. 3 is a schematic presentation of a third embodiment of the present invention.

A third embodiment of the present invention is illustrated by the apparatus 30b in FIG. 3. All of the structural elements that are identical with the previous embodiments utilize the same element numbers.

In apparatus 30b, a single detector 18 is supported on the diaphragm 13 to receiver x-ray beam 19, which passes through an aperture 20a in the aperture diaphragm or pin hole diaphragm 20. However, the diaphragm 20 is rigidly attached to the unit 3 and is not displaced therefrom. In order to scan a patient such as 7 in a vertical direction, the detector 18 for a given specific angular position of the exposing device is displaced by means 31 in the vertical direction. Simultaneously with the displacement of the detector 18, the x-ray tube 2 electronically shifts the angle of the x-ray beam 19. To this end, a ray deflection unit 21 is present and the x-ray tube 2 can be a conventional x-ray tube which has an electronic index of the x-ray beam from different targets therein. In this example, the output of the unit 21 as well as movement of the detector 18 are applied by arrows 22 and 23 to the conversion unit 11 so that the converrsion unit can coordinate the movement of the x-ray beam 19 with the movement of the detector 18.

In each of the sample embodiments discussed hereinabove it is possible to automatically adjust the distance of the radiation receiver from the jaw by means of a control system so that the magnification or enlargement of the received image is always the same. The control system of this type can be controlled with the aid of a capacitive or photoelectric detector which measures the distance from the jaw.

Although minor modifications might be suggested by those versed in the art, it should be understood that I wish to employ within the scope of the patent granted hereon all such modifications as reasonably and properly come within the scope of my contribution to the art.

I claim:

1. In a dental apparatus for x-ray diagnosis including a head support for supporting a head of a patient in a given position, and a unit having an x-ray tube and carrier for a radiation receiver, said unit being rotatable about a vertical axis with the x-ray tube and carrier rotating about the head support, said apparatus including an operative sequence mechanism for fixing the exposure time in advance as the apparatus prepares a dental survey image, the improvement comprising the radiation receiver including transducer means for measuring radiation intensities and forming electrical signals corresponding to the measured radiation intensities, said transducer means being connected to a data processing installation having means for storing electrical signals for one exposure sequence and means for creating a dental survey image from the stored electrical signals, said transducer means consisting of a plurality of detectors arranged on a vertical extending line with the number of detectors being selected to correspond to the desired image resolution, said unit further including a diaphragm with a vertically extending slit-shaped aperture disposed on the unit between the x-ray tube and the support for the head so that a beam of radiation passing through the patient has a strip shape and impinges on all detectors of the transducer means, and the apparatus including an image reproduction device connected to the data processing installation for displaying the created dental survey image.

2. In a dental apparatus for x-ray diagnosis including a head support for supporting a head of a patient in a given position, and a unit having an x-ray tube and carrier for a radiation receiver, said unit being rotatable about a vertical axis with the x-ray tube and carrier rotating about the head support, said apparatus including an operative sequence mechanism for fixing the exposure time in advance as the apparatus prepares a dental survey image, the improvement comprising the radiation receiver including transducer means for measuring radiation intensities and forming electrical signals corresponding to the measured radiation intensities, said transducer means being connected to a data processing installation having means for storing electrical signals for one exposure sequence and means for creating a dental survey image from the stored electrical signals, said transducer means consisting of a single detector, means supporting the single detector in said unit for movement in a vertical direction, said unit including a diaphragm disposed between said tube and the position of the support for the head, said diaphragm having a single aperture for limiting the size for the x-ray beam passing through the patient's head to the size of the single detector, said diaphragm being mounted for vertical movement with the transducer so that a vertical movement of the diaphragm and detector creates a vertical scan for each position of the rotating unit, and the apparatus including an image reproduction device connected to the data processing installation for displaying the created dental survey image.

3. In a dental apparatus for x-ray diagnosis including a head support for supporting a head of a patient in a given position, and a unit having an x-ray tube and carrier for a radiation receiver, said unit being rotatable about a vertical axis with the x-ray tube and carrier rotating about the head support, said apparatus including an operative sequence mechanism for fixing the exposure time in advance as the apparatus prepares a dental survey image, the improvement comprising the radiation receiver including transducer means for measuring radiation intensities and forming electrical signals corresponding to the measured radiation intensities, said transducer means being connected to a data processing installation having means for storing electrical signals for one exposure sequence and means for creating a dental survey image from the stored electrical signals, said transducer means comprising a single detector, mounting means for moving the detector along a vertical line in said unit, said unit having a diaphragm disposed between the tube and the head support, said diaphragm having an opening to limit the beam width of the x-ray passing through the patient's head to the size of said single detector, said x-ray tube having means for electronically moving the x-ray beam along a vertical path, said means for electronically moving being synchronized with said mounting means so that a vertical scanning is obtained for each position of the unit, and the apparatus including an image reproduction device connected to the data processing installation for displaying the created dental survey image.

* * * * *